United States Patent
Collinge

(10) Patent No.: US 6,998,231 B2
(45) Date of Patent: Feb. 14, 2006

(54) TYPING AND DIAGNOSIS OF SPONGIFORM ENCEPHALOPATHY

(75) Inventor: John Collinge, London (GB)

(73) Assignee: D-Gen Limited, London (GB)

( * ) Notice: Subject to any disclaimer, the term of this patent is extended or adjusted under 35 U.S.C. 154(b) by 0 days.

(21) Appl. No.: 09/778,926

(22) Filed: Feb. 6, 2001

(65) Prior Publication Data

US 2002/0081645 A1 Jun. 27, 2002

Related U.S. Application Data

(63) Continuation of application No. 09/291,215, filed on Apr. 14, 1999, now abandoned, which is a continuation of application No. PCT/GB97/02843, filed on Oct. 15, 1997.

(30) Foreign Application Priority Data

Oct. 15, 1996 (GB) ............................................. 9621469
Oct. 21, 1996 (GB) ............................................. 9621885

(51) Int. Cl.
C12Q 1/68 (2006.01)
C12N 15/00 (2006.01)
C12N 15/63 (2006.01)
C12N 1/20 (2006.01)
C07H 21/04 (2006.01)

(52) U.S. Cl. ..................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1

(58) Field of Classification Search ..................... 435/6, 435/91.1, 91.2, 7.1, 70.1, 5, 7.21; 536/24.3; 935/6; 436/518, 149, 811; 424/130, 1, 9.1, 424/9.2; 530/387.1; 548/541, 542
See application file for complete search history.

(56) References Cited

U.S. PATENT DOCUMENTS

| 4,892,814 A | * | 1/1990 | Harrington | ..................... 435/5 |
| 5,846,533 A | * | 12/1998 | Prusiner | .................. 424/130.1 |
| 6,008,435 A | * | 12/1999 | Prusiner | ..................... 800/18 |

FOREIGN PATENT DOCUMENTS

| GB | 2 258 867 | 2/1993 | |
| WO | WO 95/31466 | * 11/1995 | ................... 435/6 |
| WO | WO 96/17249 | 6/1996 | |
| WO | WO 97/04814 | 2/1997 | |
| WO | WO 97/46572 | 12/1997 | |

OTHER PUBLICATIONS

Race et al., "Proteinase K–resistant prion protein dtection in animal tissues and in vitro", Bovine Spongiform Encephalopathy The BSE Dilemma, 6tg, Williamsburg, Va., Feb. 26–Mar. 1, 1995 (1996), pp. 317–324.*

(Continued)

*Primary Examiner*—Jezia Riley
(74) *Attorney, Agent, or Firm*—Wilmer Cutler Pickering Hale and Dorr LLP

(57) ABSTRACT

The present invention relates to a method for typing a sample of a prion or spongiform encephalopathy disease, a kit suitable for use in such a typing method, a method for identifying infection in an animal and/or tissue of bovine spongiform encephalopathy (BSE), a method for assessing and/or predicting the susceptibility of an animal to BSE, a kit for use in such an assessment and/or prediction method, a method for the treatment of a prion disease, and compounds suitable for such a method.

20 Claims, 9 Drawing Sheets

OTHER PUBLICATIONS

Figure 1A:
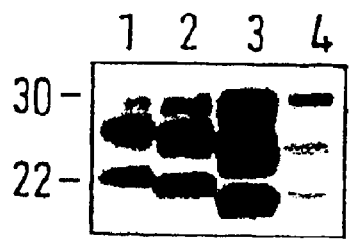
Figure 1B:
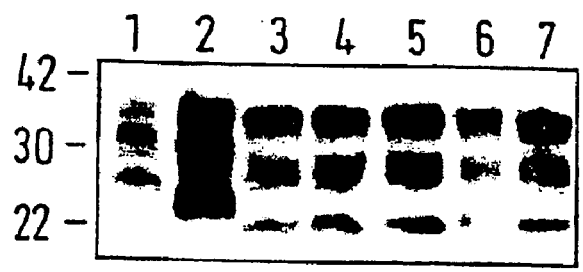

Race et al., "Diagnostic implications of detection of proteinase K–resistant protein in spleen, lymph nodes, and brain of sheep",, *American Journal of Vet Res.,* vol. 53, No. 6, pp. 883–889, 1992.*

Baker, et al., "Aminoacid polymorphism in human prion protein and age at death in inherited prion disease," Lancet, vol. 337, pp. 1286 (1991).

Bessen, et al., "Biochemical and Physical Properties of the Prion Protein from Two Strains of the Transmissible Mink Encephalopathy Agent," J. Virol., 66(12):2096–2101 (1992).

Bessen, et al., "Distinct PrP Properties Suggest the Molecular Basis of Strain Variation in Transmissible Mink Encephalopathy," J. Virol., 68(12):7859–7868 (1994).

Bessen, et al., "Non–genetic propagation of strain–specific properties of scrapie prion protein," Nature, vol. 375, pp. 698–700 (1995).

Brown, et al., "Friendly fire" in medicine: hormones, homografts, and Creutzfeldt–Jakob disease, Lancet, vol. 340, pp. 24–27 (1992).

Brown et al., "Iatrogenic Creutzfeldt–Jakob disease: An example of the interplay between ancient genes and modern medicine" Neurology, vol. 44., pp. 291–293 (1994).

Bruce, et al., "Transmission of bovine spongiform encephalopathy and scrapie to mice: strain variation and the species barrier," Phil. Trans. R. Soc. Lond. B, pp. 405–411 (1994).

Bueler, et al., "Normal development and behaviour of mice lacking the neuronal cell–surface PrP protein," Nature, vol. 356, pp. 577–582 (1992).

Carlson, et al., "Linkage of Prion Protein and Scrapie Incubation Time Genes," Cell, vol. 46, pp. 503–511 (1986).

Caughey, et al., "The Scrapie–associated Form of PrP Is Made From a Cell Surface Precursor That is Both Protease– and Phospholipase–sensitive," J. BioL. Chem., 266(27):18217–18223 (1991).

Collinge, et al., "Genetic predisposition to Iatrogenic Creutzfeldt–Jakob disease," Lancet, vol. 337., pp. 1441–1442 (1991).

Collinge, et al., "Unaltered susceptibility to BSE in transgenic mice expressing human prion protein," Nature, vol. 378, pp. 779–783 (1995).

Collinge, et al., "Prion protein gene analysis in new variant cases of Creutzfeldt–Jakob disease," Lancet, vol. 348, pp. 56 (1996).

Collinge, et al., "Molecular analysis of prion strain variation and the aetiology of 'new variant' CJD," Nature, vol. 383, pp. 685–690 (1996).

Fraser, et al., "The lymphoreticular system in the pathogenesis of scrapie," in *Prion Diseases in Humans and Animals,* Eds. Prusiner, Collinge, Powell, and Anderton, pp. 308–317 (1992).

Heckler, et al., "Replication of distinct scrapie prion isolates is region specific in brains of transgenic mice and hamsters" Genes & Development, vol. 6, pp. 1213–1228 (1992).

Kascsak, et al., "Mouse Polyclonal and Monoclonal Antibody to Scrapie–Associated Fibril Proteins," J. Virol. 61(12):3688–3693 (1987).

Kimberlin, et al., "Incubation Periods in Six Models of Intraperitoneally Injected Scrapie Depend Mainly on the Dynamics of Agent Replication within the Nervous System and Not the Lymphoreticular System" J. Gen. Virol., vol. 69, pp. 2953–2960 (1988).

Kimberlin, "The role of the spleen in the neuroinvasion of scrapie in mice," Virus Res., vol. 12, pp. 201–211 (1989).

Kocisko, et al., "Cell–free formation of protease–resistant prion protein," Nature, vol. 370, pp. 471–474 (1994).

Laemmli, "Cleavage of Structural Proteins during the Assembly of the Head of Bacteriophage T4," Nature, vol. 227, pp. 680–685 (1970).

Lasmezas, et al., "BSE transmittion to macaques" Nature, (1996), vol. 381, pp. 743–744.

Marsh et al., "Comparison of Scrapie and Transmissible Mink Encephalopathy in Hamsters. II. Clinical Signs, Pathology, and Pathogenesis," J. of Infectious Diseases, 131(2), pp. 104–110 (1975).

Masood, "Britain draws up 'superleague' plan for leading research universities," p. G, Nature, vol. 382, pp. 381 (1996).

Palmer, et al., "Homozygous prion protein genotype predisposes to sporadic Creutzfeldt–Jakob disease," Nature, vol. 352, pp. 340–342 (1991).

Palmer, et al., "Sequence Variation in Intron of Prion Protein Gene, Curcial for Complete Diagnostic Strategies," Human Mutation, vol. 7, pp. 280–281 (1996).

Pan, et al., "Conversion of $\alpha$–helices into $\beta$–sheets features in the formation of the scrapie prion proteins," Proc. Nat. Acad. Sci. USA, vol. 90, pp. 10962–10966 (1993).

Piccardo, et al., "An Antiserum to Residues 95–108 of Human PrP Detects PrPres in a Variety of Human and Animal Prion Diseases," J. Neuro. Exp. Neurol., vol. 56, pp. 589 (1997) (abstract only).

Pirola, et al., "Inhibition of scrapie–associated PrP accumulation. Probing the role of glycoaminoglycans in amyloidogenesis", Molecular Neurobiology, 8:113–120 (1994).

Prusiner, et al., "Transgenic Studies Implicate Interactions between Homologous PrP Isoforms in Scrapie Prion Replication," Cell, vol. 63, pp. 673–686 (1990).

Prusiner, S.B., "Molecular Biology of Prion Diseases," Science, vol. 252, No. 5012, pp. 1515–1522 (1991).

Schreuder, et al., "Preclinical test for prion disease," Nature, vol. 381, pp. 563 (1996).

Serban, et al., "Rapid detection of Creutzfeldt–Jakob disease and scrapie prion proteins," Neurology, vol. 40, pp. 110–117 (1990).

Telling, et al., "Transmission of Creutzfeldt–Jakob disease from humans to transgenic mice expressing chimeric human–mouse prion protein" Proc Natl Acad Sci, vol. 91, pp. 9936–9940 (1994).

Telling, et al., "Prion Propagation in Mice Expressing Human and Chimeric PrP Transgenes Implicates the Interaction of Cellular PrP with Another Protein," Cell, vol. 83, pp. 79–90 (1995).

Towbin, et al., "Electrophoretic transfer of proteins from polyacrylamide gels to nitrocellulose sheets: Procedure and some applications," Proc. Natl. Acad. Sci., 76(9):4350–4354 (1979).

Weissmann, "The prion's progress," Nature, vol. 349, pp. 569–571 (1991).

Weller, "Iatrogenic transmission of Creutzfeldt–Jakob disease," Psychol. Med., pp. 1–4 (1989).

Wells, et al., "The Neuropathology and Epidemiology of Bovine Spongiform Encephalopathy," Brain Pathol., vol. 5, pp. 91–103 (1995).

Whittington, et al., "Rescue of Neurophysiological Phenotype seen in Prp null mice by transgene encoding human prion protein," Nat. Gene., vol. 9, pp. 197–201 (1995).

Will, et al., "A new variant of Creutzfeldt–Jakob disease in the UK," Lancet, vol. 347, pp. 921–925 (1996).

Windl, et al., "Genetic basis of Creutzfeldt–Jakob disease in the United Kingdom: a systematic analysis of predisposing mutations and allelic variation in the PRNP gene" Hum. Genet., vol. 98, pp. 259–264 (1996).

Wyatt, et al., "Naturally occurring scrapie–like spongiform encephalopathy in five domestic cats," Vet. Rec., vol. 129, pp. 233–236 (1991).

Hsich, Gary, et al, "The 14–3–3 Brain Protein in Cerebrospinal Fluid as a Marker for Transmissible Spongiform Encephalopathies," The New England Journal of Medicine, 1996, vol. 335, No. 13, pp. 924–931.

Caughey, B et al., "Binding of the protease–sensitive form of PrP (prion protein) to sulfated glycosaminoglycan and congo red" (abstract) J Virol. 1994 68(4): 2135–41.

Fink, JK et al., "Detecting prion protein gene mutations by denaturing gradient gel electrophoresis" Hum Mutat. 1994 4(1): 42–50.

Laplanche, JL et al., "Molecular genetics of prion diseases in France. French Research Group on Epidemiology of Human Spongiform Encephalopathies" (abstract) Neurology 1994 44(12): 2347–51.

McKinley, MP et al., "A protease–resistant protein is a structural component of the scrapie prion" Cell, 1983 34(1): 57–62.

Parchi, P et al., "Molecular basis of phenotypic variability in sporadic Creutzfeldt–Jakob disease" Ann Neurol. 1996 39(6): 767–78.

Williamson, RA et al., "Circumventing tolerance to generate autologous monoclonal antibodies to the prion protein" Proc Natl Acad Sci U S A. 1996 93(14): 7279–82.

Xi, YG et al., "Detection of proteinase–resistant protein (PrP) in small brain tissue samples from Creutzfeldt–Jakob disease patients" J Neurol Sci. 1994 124(2): 171–3.

Caughey, B. et al. "Binding of the Protease–Sensitive Form of Prion Protein PrP to Sulfated Glycosaminoglycan and Congo Red." J. of Virology 1994; 68(4):2135–41.

Fink, J.K. et al., "Detecting Prion Protein Gene Mutations by Denaturing Gradient Gel Electrophoresis." Human Mutation 4(1994):42–50.

Laplanche, J.L. et al. "Molecular genetics of prion diseases in France." Neurology 44(1994):2347–51.

McKinley, M.P. et al. "A Protease–Resistant Protein is a Structural Component of the Scrapie Prion." Cell 35(1983):57–62.

Parchi, P. et al. "Molecular Basis of Phenotypic Variability in Sporadic Creutzfeldt–Jakob Disease." Annals of Neurology 1996; 39(6):767–77.

Williamson, R.A. et al. "Circumventing tolerance to generate autologous monoclonal antibodies to the prion protein." Proc. Natl. Acad. Sci. USA 93(1996):7279–82.

Xi, Y.G. et al. "Detection of proteinase–resistant protein (PrP) in small brain tissue samples from Creutzfeldt–Jakob disease patients." J. of Neurological Sci. 124(1994):171–73.

* cited by examiner

TABLE 1

| CLASSIFICATION | CODON 129 GENOTYPE | TYPE 1 | TYPE 2 | TYPE 3 | TYPE 4 | TOTAL |
|---|---|---|---|---|---|---|
| SPORADIC | MM | 5 | 13 | 0 | 0 | 18 |
| SPORADIC | MV | 0 | 4 | 0 | 0 | 4 |
| SPORADIC | VV | 0 | 4 | 0 | 0 | 4 |
| IATROGENIC (GROWTH HORMONE) | MM | 1 | 0 | 0 | 0 | 1 |
| IATROGENIC (GROWTH HORMONE) | MV | 0 | 0 | 1 | 0 | 1 |
| IATROGENIC (GROWTH HORMONE) | VV | 0 | 0 | 3 | 0 | 3 |
| IATROGENIC (GONADOTROPHIN) | VV | 0 | 0 | 1 | 0 | 1 |
| IATROGENIC (DURA MATER) | MM | 0 | 1 | 0 | 0 | 1 |
| "NEW VARIANT" | MM | 0 | 0 | 0 | 10 | 10 |

TABLE 2

INCUBATION PERIODS FOR TRANSMISSION OF PRION DISEASES TO TRANSGENIC AND WILD-TYPE MICE.

| | | | TRANSGENIC | | WILD-TYPE | |
|---|---|---|---|---|---|---|
| TYPE OF INOCULUM | PRNP CODON 129 | No. OF INOCULA | AFFECTED / INOCULATED | INCUBATION PERIOD (DAYS) | AFFECTED / INOCULATED | INCUBATION PERIOD (DAYS) |
| spCD | MM | 9 | 66 / 67 | 210 ± 04 | 0 / 60 | >450 OR >600 |
| spCJD | VV | 1 | 5 / 5 | 337 ± 11 | 1 / 5 | 471 |
| spCJD | MV | 2 | 15 / 15 | 218 ± 2 | 1 / 9 | 257 |
| iCJD (GH) | MM | 1 | 7 / 7 | 211 ± 5 | 1 / 5 | 318 |
| iCJD (GH) | MV | 1 | 4 / 4 | 195 ± 9 | 1 / 5 | 387 |
| iCJD (GH) | VV | 1 | 5 / 5 | 193 ± 4 | 0 / 5 | >600 |
| iCJD (DM) | MM | 1 | 4 / 4 | 204 ± 6 | 2 / 4 | 569, 569 |
| iCJD (G) | VV | 1 | 8 / 8 | 187 ± 4 | 0 / 5 | >600 |
| vCJD | MM | 6 | 25 / 56 | 228 ± 15 | 33 / 43 | 371 ± 17 |
| BSE | | 5 | 10 / 26 | 602 ± 50 | 21 / 24 | 466 ± 26 |

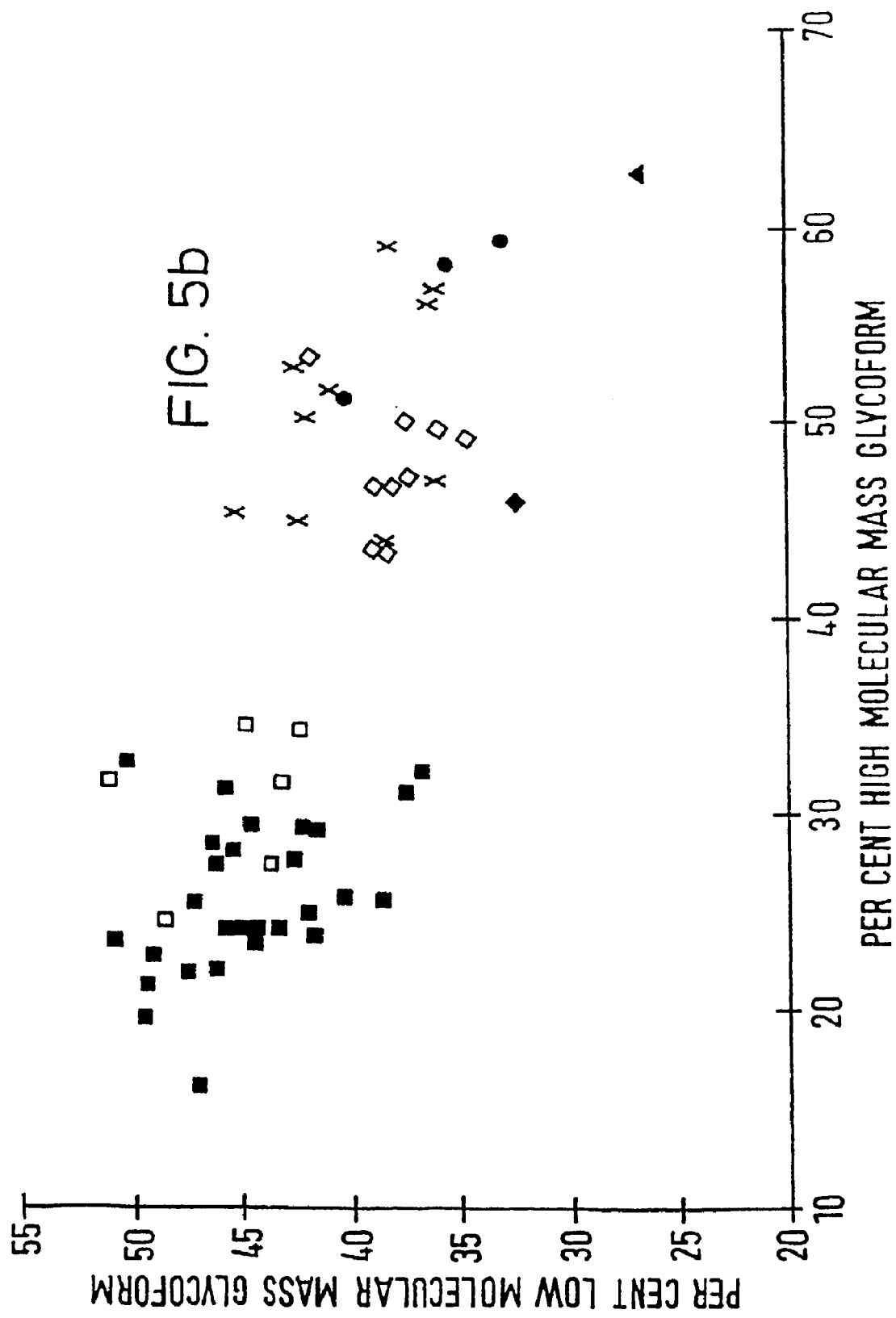

```
SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gttttccagg cccatcagtg                                                20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctatgcactc attcattatg c                                              21
```

TYPING AND DIAGNOSIS OF SPONGIFORM ENCEPHALOPATHY

CROSS-REFERENCE TO RELATED APPLICATION

This application is a continuation of U.S. patent application Ser. No. 09/291,215, filed Apr. 14, 1999, now abandoned, which is a continuation of PCT/GB97/02843, filed Oct. 15, 1997, which claims priority to GB 9621469.7, filed Oct. 15, 1996 and GB 9621885.4, filed Oct. 21, 1996.

The present invention relates to a method for typing a sample of a prion or spongiform encephalopathy disease, a kit suitable for use in such a typing method, a method for identifying infection in an animal and/or tissue of bovine spongiform encephalopathy (BSE), a method for assessing and/or predicting the susceptibility of an animal to BSE, a kit for use in such an assessment and/or prediction method, a method for the treatment of a prion disease, compounds suitable for such a method, use of such compounds and pharmaceutical agents comprising such compounds. In particular, the present invention relates to the molecular analysis of prion strain variation and the aetiology of "new variant" Creutzfeldt-Jakob disease.

The prion diseases or transmissible spongiform encephalopathies are a group of neurodegenerative diseases that affect both humans and animals and which can be transmitted between mammals by inoculation with, or in some cases dietary exposure to, infected tissues. They are associated with the accumulation in affected brains of an abnormal isoform of a host encoded glycoprotein, prion protein (PrP), which appears to be the central and possibly the sole component of the transmissible agent or prion[1]. This disease related isoform, $PrP^{Sc}$, can be distinguished from the normal cellular isoform, $PrP^{C}$, by its insolubility and partial resistance to proteases. $PrP^{Sc}$ is derived from $PrP^{C}$ by a post-translational mechanism[2] which appears to involve a conformational, rather than covalent, modification[3]. Transgenic, human molecular genetic and in vitro conversion studies support a model for prion propagation which involves a direct protein protein interaction between host $PrP^{C}$ and inoculated $PrP^{Sc}$, with $PrP^{Sc}$ acting to promote conversion of $PrP^{C}$ to further $PrP^{Sc}$ in an autocatalytic process which proceeds most efficiently when the interacting proteins are of identical primary structure[4-7]. In addition to the unique biology of these diseases, interest in them has been intensified because of the epidemic of a novel prion disease, bovine spongiform encephalopathy (BSE)[8], in the UK and now in other countries and the possibility that this may represent a significant threat to public health through ingestion of BSE infected tissues. BSE is known to have caused prion disease in a number of other species, including domestic cats (feline spongiform encephalopathy) and captive exotic ungulates (nyala and kudu), presumably as a result of ingestion of BSE contaminated feed[9]. The pathogenicity of bovine prions for humans is unknown, although the results of challenge of transgenic mice expressing human prion protein, which lack a species barrier to human prions, suggest that induction of human prion production by bovine prions is inefficient[10].

Although many converging lines of evidence support the "protein only" hypothesis for prion propagation[1], the existence of multiple distinct isolates or "strains" of agent which can be stably passed in inbred mice of the same prion protein genotype has yet to be satisfactorily explained within this model. Strains can be distinguished by their different incubation periods and patterns of neuropathology when passaged in mice[11]. A number of distinct strains of natural sheep scrapie are recognized, for instance, while BSE appears to be caused by a single strain of agent[9]. Support for the contention that strain specificity is encoded by PrP alone is provided by study of two distinct strains of transmissible mink encephalopathy prions which can be serially propagated in hamsters, designated hyper (HY) and drowsy (DY)[12]. The strains can be distinguished by differing physicochemical properties of the accumulated $PrP^{Sc}$ in the brains of affected hamsters[13]. Following limited proteolysis, strain specific migration patterns of $PrP^{Sc}$ on polyacrylamide gels can be seen. DY $PrP^{Sc}$ appears to be more protease sensitive than HY $PrP^{Sc}$, producing a different banding pattern of $PrP^{Sc}$ on Western blots following proteinase K treatment. This relates to different N-terminal ends of HY and DY $PrP^{Sc}$ following protease treatment and implies differing conformations of HY and DY $PrP^{Sc}$ [14]. Furthermore, the demonstration that these strain specific physicochemical properties can be maintained during in vitro production of protease resistant PrP, when $PrP^{C}$ is mixed with HY or DY hamster $PrP^{Sc}$, further supports the concept that prion strains involve different PrP conformers[15].

The human prion diseases occur in inherited, acquired and sporadic forms. Around 15% are inherited, associated with coding mutations in the prion protein gene (PRNP)[16]. Acquired prion diseases include kuru and iatrogenic CJD. Recognised iatrogenic routes of transmission are treatment with human cadaveric pituitary derived growth hormone or gonadotrophin, dura mater or corneal grafting and the use of inadequately sterilised neurosurgical instruments[17]. However, the large majority of human prion disease occurs as sporadic CJD, where pathogenic PRNP mutations and a history of iatrogenic exposure are absent. The large majority of sporadic CJD cases are homozygous at polymorphic residue 129, a common protein polymorphism in human PrP that is known to play a key role in genetic susceptibility to human prion diseases[6,16,18-20]. Recently, Will et al reported the occurrence of a novel form of human prion disease in the UK, affecting unusually young people and having a highly consistent and unique clinicopathological pattern[21]. To date, all patients studied are homozygotes (for methionine) at polymorphic residue 129 of PrP and no coding mutations are present[22]. None have a history of iatrogenic exposure to human prions. This may indicate the arrival of a new risk factor for CJD in the UK and dietary exposure to specified bovine offals, prior to their statutory exclusion from the human diet in the UK in 1989, seems to be the most likely candidate. The risk of susceptability to BSE or a variation or related disease is, at present, believed to be greatest for individuals whom are homozygous at polymorphic residue 129 of PrP (and homozygous for methionine a greater risk than valine). It is unknown how many strains of human prions cause Creutzfeldt-Jakob disease (CJD); only two distinct patterns of protease resistant PrP have been reported to date, associated with different clinicopathological types of sporadic CJD[23].

Accordingly, a first aspect of the invention provides a method for typing a sample of a prion or spongiform encephalopathy disease the method comprising comparing and/or identifying similar physiochemical properties of the sample with a standard sample of known type. The standard sample of a known type may be any of those known in the art, or future samples of a known type. This standard sample of a known type may be bovine spongiform encephalopathy or Creutzfeldt-Jakob disease.

Comparing and/or identifying similar physicochemical properties (unless including dissimilar physicochemical properties) are well known techniques in the art. Comparison of any physicochemical properties can be used, for example a comparison of protease resistance and/or glycoform ratios. A suitable protease resistance comparison is proteinase K resistance.

The standard sample of known type may be a bovine spongiform encephalopathy sample which is bovine or non-bovine derived. In particular, the bovine spongiform encephalopathy may be mammalian or chicken derived, or feline, ovine, cervine, human or other primate (suitably macaque) or murine derived.

The method for typing a sample of a prion or a spongiform encephalopathy disease may comprise the steps of subjecting the sample to digestion via proteases, electrophoresing the results of the digestion step and comparing the resulting pattern of the electrophoresis with a standard electrophoresis of a known sample. Similar and/or slightly varied methods are common well known techniques used constantly in the art.

A method for typing a sample of a prion or a spongiform encephalopathy disease, according to the invention, may comprise a method of diagnosing a disease. The method, whether it be for the diagnosis of a disease or not, may involve a sample which is mammalian or chicken derived, in particular derived from a human, (or other primate-suitably macaqque) bovine, ovine, macaque, cervine or murine animal.

The sample to be typed is preferably derived from brain tissue, other central nervous system tissue, a tissue of the lymphoreticular system (including the spleen, tonsil or lymph node), cerebrospinal fluid and/or the blood. A sample from one or more individual tissues may be used according to the present invention.

Figure 4:
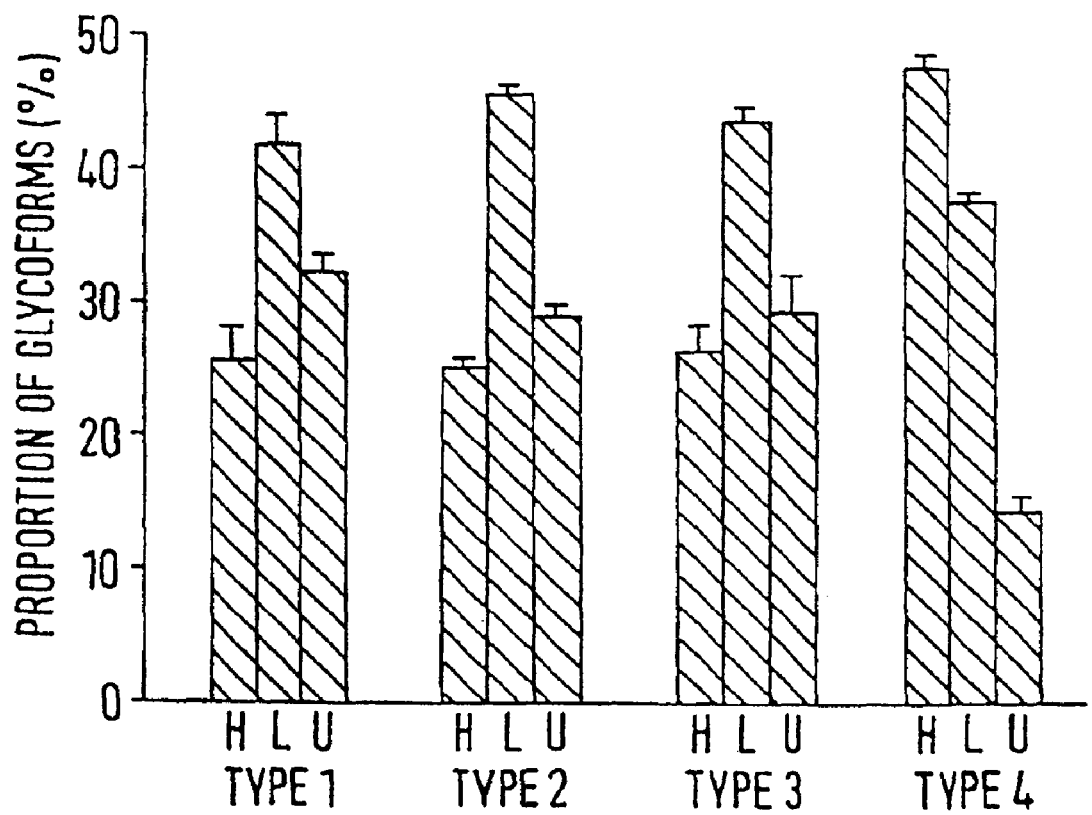

In the methods according to the first aspect of the invention, the electrophoresis pattern of the known sample may have a pattern substantially similar to that of type 4 as shown in FIG. 4 or an equivalent pattern when electrophoresed under varied conditions.

A second aspect of the invention provides a kit for typing a prion or spongiform encephalopathy sample or diagnosing a prion or spongiform encephalopathy disease, the kit comprising a prion or encephalopathy electrophoresis gel standard. Optionally the kit may include means to provide comparison of physiochemical properties of the samples to be typed and the gel standard. Such means include a protease enzyme, such as proteinase K. The kit may comprise the gel standard and optional other ingredients in combination with instructions for using the kit and/or packaging means, such as a container.

A third aspect of the invention provides a method for identifying infection in an animal and/or tissue of bovine spongiform encephalopathy, the method comprising isolating a prion protein from the animal and/or tissue and identifying that said prion protein can be characterised by having three distinct bands on an electrophoresis gel following proteinase K digestion, the bands comprising i) a band of highest molecular weight in the greatest proportion, ii) a band of lowest molecular weight in the lowest proportion, and iii) a band with a molecular weight between i an ii and of a proportion between i and ii or characterised by having substantial similar glycoform proportions as bovine spongiform encephalopathy. In the method according to the third aspect, the animal and/or tissue from which the prion is sampled may be mammalian or chicken derived, and in particular human, (or other primate-suitably macque) ovine or murine derived. The prion sample may be derived from one or more of the following: brain tissue, other central nervous system tissue, a tissue of the lymphoreticular system (including the spleen, tonsil or lymph node), cerebrospinal fluid and/or the blood.

A fourth aspect of the invention provides a method for assessing and/or predicting the susceptibility of an animal, in particular a human individual, to bovine spongiform encephalopathy or a derivative thereof, the method comprising the step of determining the genotype of the individual at polymorphic residue 129 of PrP. The determination may be whether the individual is homozygous or heterozygous at polymorphic residue 129 of PrP, in particular whether the animal is homozygous for methionine or valine at polymorphic residue $^{129}$ of PrP. The most susceptible genotype to bovine spongiform encephalopathy, to date, is homozygous for methionine (MM). This genotype appears. in approximately 38% of the UK population. Other susceptible genotypes, in order of decreasing susceptibility are valine/valine homozygotes and methionine/valine heterozygotes. The method of the fourth aspect of the invention may be carried out using DNA obtained from a biological sample of the animal, in particular where the biological sample is blood.

A fifth aspect of the invention relates to a kit for use in assessing and/or predicting the susceptibility of an animal, in particular a human individual, to bovine spongiform encephalopathy or a derivative thereof, which comprises at least one pair of primers suitable for PCR amplification of at least a portion of the gene coding for PrP. Suitable primers include (SEQ ID NO:1)
5'-GTTTTCCAGGCCCATCAGTG-3'

(SEQ ID NO:2)
5'-CTATGCACTCATTCATTATGC-3'

We have investigated a wide range of cases of human prion disease to identify patterns of protease resistant PrP that might indicate different, naturally occurring, prion strain types. We then studied "new variant" CJD to determine whether it represents a distinct strain type that can be differentiated on molecular criteria from other forms of CJD. Here we demonstrate that sporadic and iatrogenic CJD is associated with three distinct patterns of protease resistant PrP on Western blots. Types 1 and 2, as previously described, are seen in sporadic CJD, and also in some iatrogenic CJD cases. A third type is seen in acquired prion diseases that arise from a peripheral route of exposure to prions. "New variant" CJD is associated with a unique and highly consistent appearance of protease resistant PrP on Western blots involving a characteristic pattern of glycosylation. While transmission of CJD to inbred mice produces a pattern characteristic of the inoculated CJD, transmission of BSE produces a glycoform ratio pattern closely similar to "new variant" CJD. Similarly, experimental BSE in macaque and naturally acquired BSE in domestic cat shows an indistinguishable glycoform pattern to experimental murine BSE and "new variant" CJD. Transmission of type 1, 2 and 3 CJD to transgenic mice expressing human PrP reveal persistence or conversion of strain type dependent on PRNP codon 129 genotype, providing supportive evidence for the "protein only" hypothesis of infectivity and suggesting that strain variation may be encoded by a combination of PrP conformation and glycosylation.

Accordingly, the present invention provides methods of typing, diagnosis, identifying infection and kits as set out in the claims and in the description.

Sporadic and Acquired CJD

Figure 1C:
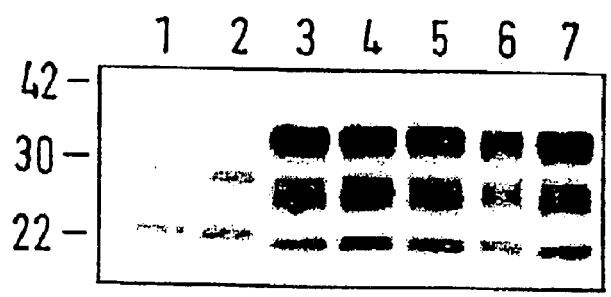

Typically three bands are seen on Western blots of protease resistant PrP from CJD cases. The two larger molecular weight bands represent the major glycosylated forms of PrP while the smaller band represents unglycosylated PrP[23] (FIG. 1). Parchi et al, described two distinct patterns in sporadic CJD: a type 1 pattern was seen in the majority of CJD cases with homozygosity for methionine (MM) at polymorphic residue 129 of PrP; a type 2 pattern was seen in a minority of MM cases and in all methionine/valine heterozygotes (MV) and valine homozygotes (VV)[23]. We performed Western blot analysis of protease resistant prion proteins on a total of 26 neuropathologically confirmed sporadic CJD cases representing all three PRNP codon 129 genotypes; cases both pre-dating and contemporary with the bovine spongiform encephalopathy epidemic were included (table 1). We confirmed the finding of Parchi et al[23] that in sporadic CJD, MM cases had two distinct banding patterns (designated types 1 and 2) (FIGS. 1a and b and table 1), while VV and MV cases all showed the type 2 banding pattern[23] (FIG. 1c and table 1). In our sample of sporadic CJD, we found type 2 MM to be more frequent than type 1 MM (table 1). In addition, Parchi et al noted differences in the propFlortion of protease resistant PrP in each of the three bands between the type 1 and type 2 sporadic CJD patients[23]. In our larger series, a statistically significant difference was seen between type 1 and type 2 cases with respect to the proportion of the low molecular weight glycoform, but not with respect to the other two bands (FIG. 4 legend).

We then studied a range of iatrogenic CJD, including human pituitary derived growth hormone patients with all three PRNP codon 129 genotypes, a human pituitary derived gonadotrophin patient and a patient who developed CJD following a dura mater graft.

Figure 2:
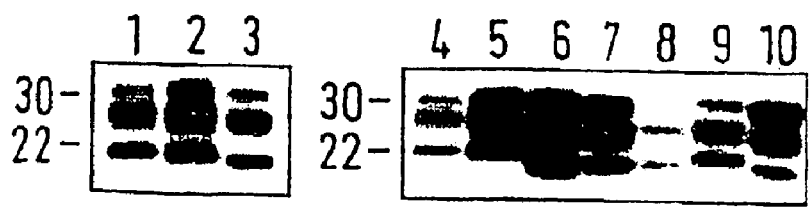

A third, distinct banding pattern of protease resistant PrP was detected in all the pituitary hormone related cases which were of PRNP codon 129 genotype MV or VV (FIG. 2). In this "type 3" pattern all three bands are shifted, consistent with an approximately 2–3 kDa decrease in size of the protease resistant PrP detected as compared to type 2 sporadic CJD. There were no significant differences in glycoform ratios between type 1 and type 3 or between type 2 and type 3 CJD in this sample (FIG. 4 legend). The single MM growth hormone case had a banding pattern indistinguishable on Western blot analysis from type 1 sporadic CJD cases (FIG. 2). The dura mater related case had a banding pattern indistinguishable from type 2 sporadic CJD (FIG. 2). The possibility that there may be further heterogeneity within individual PrP$^{Sc}$ types is under investigation.

Transmission Studies to Mice

Figure 3:
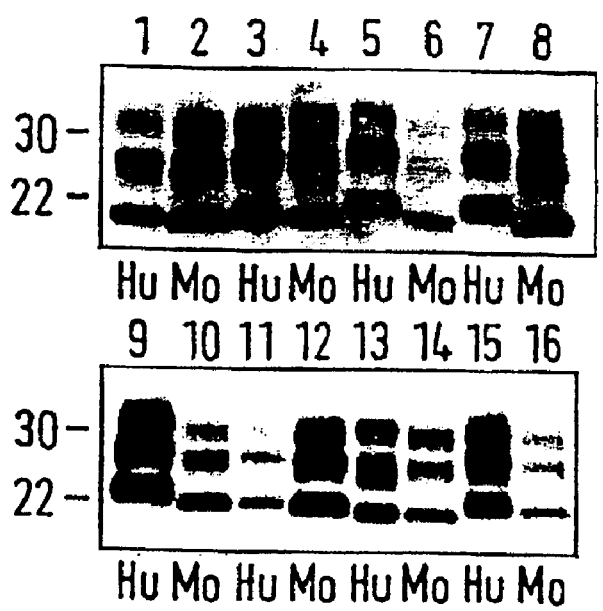

We are studying the transmission characteristics of CJD in transgenic mice which express human PrP but not murine PrP (designated HuPrP$^{+/+}$ Prn-p$^{0/0}$ as they are homozygous for the human transgene array)[10]. These mice lack a species barrier to human prions and most or all inoculated mice succumb to prion disease with consistently short incubation periods[10, 24] usually in the region of 180–220 days (data not shown). This is in marked distinction to studies with non-transgenic mice using the same inocula where transmissions are infrequent and when they occur are associated with prolonged and variable incubation periods. Transmission of type 2 CJD (of all three codon 129 genotypes) or type 3 CJD (which were all of genotype MV or VV) resulted in production of protease resistant human PrP in the mice with an identical banding pattern to the primary inoculum (that is type 2 or 3 respectively) (FIG. 3). The HuPrP$^{+/+}$ Pn-p$^{0/0}$ mice used encode valine at residue 129[25]. However, transmission of type 1 CJD (which are all of genotype MM) resulted consistently in a type 2 banding pattern of human protease resistant PrP produced in the mice (FIG. 3).

The proportion of different glycoforms on Western blots of brain homogenates from these mice was indistinguishable from that of the human cases themselves (data not shown).

New Variant CJD

Figure 1D:
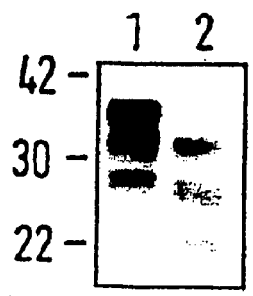
Figure 1E:
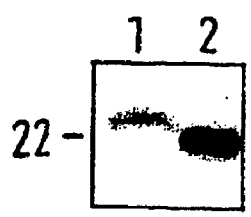
Figure 5A:
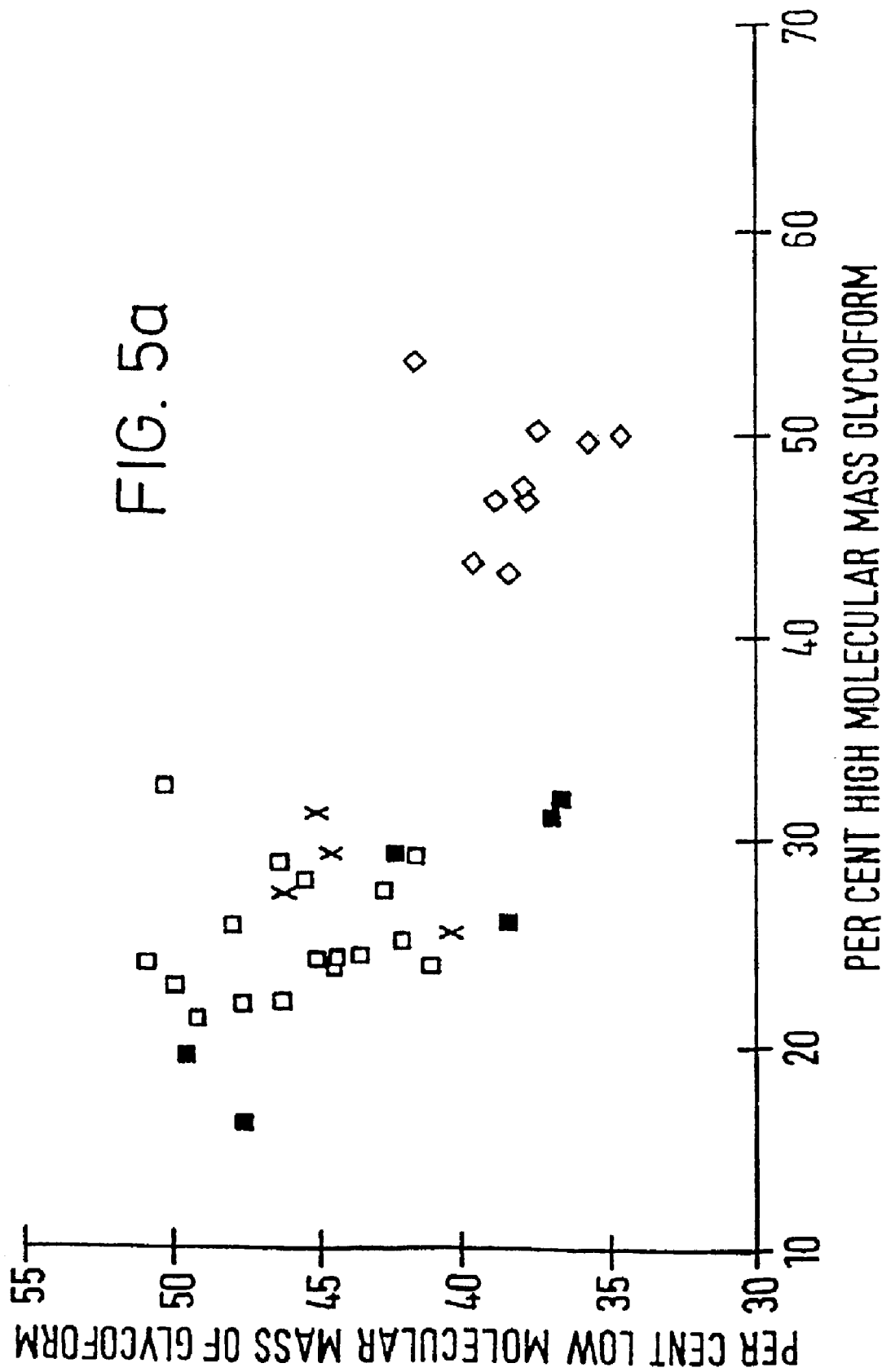

Proteinase K treatment of PrP$^{Sc}$ from "new variant" CJD revealed the characteristic band shift seen after digestion to the protease resistant fragment, confirming complete digestion of the protease sensitive N-terminal region of PrP$^{Sc}$ in the conditions used (FIG. 1d). All patients with "new variant" CJD studied were homozygotes for methionine at polymorphic residue 129[22]. No known or novel coding mutations of PRNP were seen in the "new variant" CJD cases or the sporadic CJD cases sequenced. Western blot analysis of these ten "new variant" CJD cases revealed a consistent and distinct pattern of protease resistant PrP forms, which could be clearly differentiated by band sizes from type 1 and type 2 sporadic CJD cases (FIG. 1, a–c), and from type 3 CJD by a striking and distinctive pattern of band intensities which differed from all three CJD types (FIG. 4). Deglycosylation with PNGaseF resulted in a single band suggesting a consistent proteolytic cleavage site irrespective of glycosylation state (FIG. 1e) and which differs from that seen in sporadic CJD. The high molecular weight glycoform was the most abundant with relatively little unglycosylated PrP when compared to type 1, type 2 and type 3 CJD. These differences in band intensity to types 1–3 CJD were all highly statistically significant (FIG. 4 legend). A scattergram of the relative proportions of the high molecular weight glycoform and the low molecular weight glycoform reveals two non-overlapping populations of cases: "new variant" CJD has a distinctive pattern that differs markedly from all previously recognised types of sporadic and iatrogenic CJD (FIG. 5a).

Comparison with BSE

Figure 6:
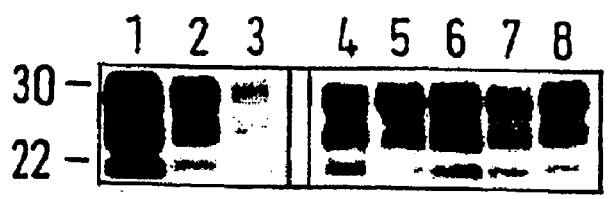

As the band intensities of protease resistant PrP in "new variant" CJD differed markedly from sporadic and iatrogenic CJD we investigated if this distinctive glycoform pattern was also seen in naturally or experimentally transmitted BSE. Firstly, we compared transmissions of BSE and CJD to the same inbred mice. Comparative transmission data in transgenic mice was not available as BSE has not transmitted, to date, to HuPrP$^{+/+}$ Prn-p$^{0/0}$ mice (>500 days post-inoculation). The glycoform ratios seen in CJD transmissions to wild type FVB mice were indistinguishable from those of the three types of CJD (FIG. 5b). However, BSE transmission into both wild type FVB and C57BL/6 mice resulted in ratios which were closely similar to those of "new variant" CJD (FIG. 5b and FIG. 6). Similarly, band sizes of protease resistant PrP seen on transmission of BSE to wild type mice were shifted to a lower molecular mass as compared to type 2 CJD transmissions (data not shown). We then studied naturally transmitted BSE in domestic cat (feline spongiform encephalopathy[26]) and experimental BSE in a macaque[27]. These cases also closely resembled "new variant" CJD and experimental murine BSE (FIG. 7a and FIG. 5b). BSE itself was not detectable on Western blots using the 3F4 monoclonal (available from Senetek Plc, Senescence Technology, Maryland Heights, Mo., USA) or R073 polyclonal antibody. However, a PrP$^{Sc}$ signal was detected from homogenates of brainstem from naturally infected BSE using a rabbit antibody to a synthetic human PrP peptide (95–108) and the pattern of the glycoforms (% high MW 51.2, % low MW 33.9, % unglycosylated 14.9)

was closely similar to transmitted BSE and "new variant" CJD. This antibody also detected PrP$^{Sc}$ from domestic cat, macaque and humans, producing similar results to R073 and 3F4 antisera (data not shown).

Discussion

Sporadic and iatrogenic CJD seems to be related to production of three distinct types of human PrP$^{Sc}$ which can be differentiated on Western blots following proteolytic cleavage by differing band sizes. Types 1 and 2 are associated with different clinicopathological phenotypes of sporadic CJD[23] and type 3 is seen in cases of iatrogenic CJD where exposure to prions has been via a peripheral route (intramuscular injection of human cadaveric pituitary-derived hormones) rather than by a direct CNS route (dura mater grafting). It is well recognised that such peripherally acquired cases have a distinct phenotype, presenting with cerebellar ataxia and psychiatric disturbance rather than as a dementing illness[28]. Iatrogenic CJD resulting from CNS exposure typically resembles classical sporadic CJD[28]. New variant CJD, while having PrP$^{Sc}$ band sizes similar to type 3 CJD, can be distinguished from all three types of CJD by a characteristic pattern of band intensities. This distinctive molecular marker, which clearly differentiates "new variant" CJD from sporadic CJD, serves to support the proposal, based on comparative clinicopathological studies and epidemiological surveillance[21], that "new variant" CJD is a distinct and novel sub-type of prion disease, related to a previously unrecognised prion strain. The limited number of different human PrP$^{Sc}$ types makes the spontaneous occurrence of a novel type that is the same in twelve individuals in the UK over the last two years extraordinarily unlikely as an explanation for "new variant" CJD. The alternative conclusion is that these cases have arisen from a common source of exposure to a new prion strain, and the lack of any history of common iatrogenic exposure suggests that this is a novel animal strain. That the glycoform "signature" of "new variant" CJD is seen in BSE itself, experimental murine BSE (while CJD transmission to these types of mice produces the CJD "signature") and in naturally transmitted BSE in domestic cat and experimental BSE in macaque, is consistent with the hypothesis that "new variant" CJD results from BSE transmission to humans. Transmission studies of "new variant" CJD in HuPrP$^{+/+}$ Pm-P$^{0/0}$ mice are in progress; it will be of interest to compare incubation periods and patterns of neuropathology with other CJD transmissions (which are also currently under study). PrP$^{Sc}$ typing will be of immediate application in wider epidemiological studies of CJD: it is possible that BSE could produce other clinicopathogical phenotypes in humans, particularly in different age groups and different ethnic populations, that are not recognised as "new variant" CJD. Furthermore, this method may also allow typing of various animals to see if BSE has also transmitted naturally to these species. There is particular concern that BSE may have transmitted to, and be being maintained in, the sheep population[29]. Typing of known scrapie strains which predated the BSE epidemic, and recent isolates, will be important in this regard.

This molecular marker can already be used in differential diagnosis of "new variant" CJD. "New variant" CJD is atypical both in its clinical features and electroencephalogram, such that diagnosis is dependent on neuropathology, either at autopsy or in some cases on brain biopsy. However, although the brain biopsy may demonstrate spongiform encephalopathy and PrP immunoreactivity adequate for a diagnosis of CJD, the characteristic neuropathological features necessary for a diagnosis of "new variant" CJD may not be present in the biopsy sample[21]. As PrP is expressed in the lymphoreticular system and prion replication occurs in spleen and in other lymphoreticular tissues[30], it may be possible to detect this molecular marker of "new variant" CJD in tonsil[31] or lymph node biopsy and thereby avoid brain biopsy.

The aetiology of sporadic CJD remains unclear but may involve somatic PRNP mutation or spontaneous conversion of PrP$^C$ to PrP$^{Sc}$ as a rare stochastic event. Sporadic CJD is associated with type 1 or type 2 PrP$^{Sc}$. Type 1 is always associated with genotype MM, type 2 with all genotypes (MM, MV or VV). Type 3 is seen in iatrogenic CJD of genotype MV or VV. Only human PrP M129 appears to form type 1 PrP$^{Sc}$ while either human PrP M129 or human PrP V129 can produce type 2 PrP$^{Sc}$.

Since type 3 PrP$^{Sc}$ is only seen in MV or VV individuals, it is possible that only human PrP V129 can form this type. As type 3 PrP$^{Sc}$ is seen in peripherally acquired iatrogenic CJD cases it is possible that this strain is selected in or preferentially produced by the lymphoreticular system, where prion replication occurs first in experimentally transmitted disease in mice[32]. If such a PrP$^{Sc}$ type was formed preferentially from human PrP V129 this could explain the excess of the PRNP codon 129 VV genotype amongst pituitary hormone related CJD cases[19, 20, 33]. Further studies will be required to determine if the type 3 pattern is a consistent marker of peripheral, as opposed to central prion exposure or sporadic CJD. It is of note, however, that similar sizes of bands are seen in the type 4 ("new variant" CJD) pattern (which are of PRNP genotype MM), which appears to have arisen by peripheral (presumably dietary) exposure to bovine prions. The formation of particular PrP$^{Sc}$ types appears to be constrained by host PRNP codon 129 genotype. This finding is supported by the observation that type 1 PrP$^{Sc}$ converts to type 2 on passage in transgenic mice expressing human PrP encoding valine at residue 129, while types 2 and 3 remain unchanged on such passage.

That different types of human PrP$^{Sc}$ are seen in association with distinct clinicopathological phenotypes of CJD, and can be maintained on passage in mice, argues that these represent distinct human prion strains. The finding that strains appear to involve different post-translational modifications of PrP which persist or (when PrP genotypes are mismatched) can be predictably converted between discrete strains on passage in mice is consistent with a "protein only" model of prion propagation in which strains are encoded by post-translational modification of PrP itself without the need for a nucleic acid or other co-factor. The bands seen on Western analysis of PrP following proteolytic cleavage represent diglycosylated, monoglycosylated (at either of the two N linked glycosylation sites[34]) and unglycosylated PrP, and two separate features of these bands, shifts in mobility and differences in relative intensities, appear to be associated with strain type. The mobility shifts after cleavage, seen in all three bands, imply different PrP conformations (which may include differing states of assembly). The differences in glycoform ratios could indicate preferential conversion of particular glycoforms into particular conformational states. It has been argued that differing PrP glycosylation in different brain regions could provide a mechanism for the targetting of neuropathology seen with different strain types, as prions may replicate most efficiently in cell populations expressing a similarly glycosylated PrP on the cell surface. Both PrP conformation and glycosylation may contribute to strain type but further studies will be required to investigate whether these two post-translational modifications of PrP can contribute to strain type independently, or are closely coupled phenomena.

The present invention describes altered patterns of glycosylation that are involved in prion diseases and, in particular, distinguish bovine spongiform encephalopathy and new variant Creuztfeldt-Jakob disease from other, forms of Creuztfeldt-Jakob disease. It is possible that particular glycosylated forms of PrP are involved in the production of, or the stability of, the disease related isoforms of PrP. Thus, inhibitors of the biosynthetic processing pathway for sugars attached to glycoproteins will inhibit prion replication and can therefore be used to form the basis of therapeutic agents for animal and human prion disease.

Accordingly, a sixth aspect of the present invention provides a method for the prevention or treatment of a prion disease by administration of a compound which inhibits the attachment of sugars to proteins and glycoproteins.

The present invention also provides, according to a seventh aspect, a pharmaceutical agent comprising a compound which inhibits the attachment of sugars to a protein or a glycoprotein in combination with a pharmaceutically acceptable carrier.

The present invention also provides according to an eighth aspect, a compound which inhibits the attachment of sugars to proteins or glycoproteins for use as an active pharmaceutical substance.

The compound is particularly useful in the prevention and/or treatment of a prion disease. The prion diseases to be treated include any such disease known in the art and include bovine spongiform encephalopathy and Creuztfeldt-Jakob disease (including "new variant" Creuztfeldt-Jakob disease described in this application) in both bovine, human and other animals.

The compound may be administered for such use in a pharmaceutically acceptable excipient, optionally together with one or more other pharmaceutically active agents.

Many such inhibitors of sugar attachment to proteins and glycoproteins are known in the art. One example is deoxynojirimycin and any of its derivatives.

The present invention also provides, according to a ninth aspect, the use of a compound which inhibits the attachment of sugars to proteins or glycoproteins in the manufacture of a medicament for the prevention or treatment of a prion disease. The prion disease to be treated is as described above.

The administration of such a compound in the prevention or treatment of a prion disease must either be administered direct to the infected tissue, or is preferably a compound which is able to cross the blood-brain barrier. The therapeutic agent, advantageously can be administered orally, rectally or topically and can be administered for the remainder of the patient's life.

All features, including preferred features of individual aspects of the invention as described above, apply to other aspects of the invention.

The invention will now be described by way of the following non-limiting examples which are provided for the purposes of illustration, and with reference to the accompanying drawings in which:

TABLE 1 shows the distribution of PRNP genotypes and banding type of protease resistant PrP in neuropathogically confirmed sporadic, iatrogenic and "new variant" CJD cases. MM=methionine homozygous genotype at PRNP codon 129; MV and VV refers to methionine/valine heterozygotes and valine homozygotes respectively.

TABLE 2 shows the incubation periods for transmission of prion diseases to transgenic and wild-type mice.

FIG. 1 shows western blots of proteinase K treated brain homogenates from patients with sporadic and "new variant" CJD using anti-PrP monoclonal antibody 3F4. Numbers adjacent to horizontal bars indicate positions of molecular weight markers (kilodaltons). (a) Lane 1, type 1 sporadic CJD, PRNP genotype MM; lane 2, type 2 sporadic CJD, PRNP genotype MM; lane 3, type 3 iatrogenic CJD, PRNP genotype VV; lane 4, "new variant" CJD, PRNP genotype MM, "type 4" banding pattern. (b) Lanes 1 and 2, type 1 and type 2 sporadic CJD respectively (both with PRNP MM genotype; lanes 3–7 "new variant" CJD cases (all PRNP genotype MM). (c) Lane 1, type 2 sporadic CJD, PRNP genotype MV; lane 2, type 2 sporadic CJD, PRNP genotype VV; lanes 3–7, "new variant" CJD (all PRNP genotype MM). (d) "new variant" CJD before (1) and after (2) treatment with proteinase K. (e) Western blot of deglycosylated PrP. Lane 1, type 2 sporadic CJD, PRNP genotype MM; lane 2, "new variant" CJD, PRNP genotype MM. Number adjacent to horizontal bars indicates position of molecular weight marker (kilodaltons).

FIG. 2 shows western blots of proteinase K treated brain homogenates from patients with iatrogenic CJD using anti-PrP monoclonal antibody 3F4. Numbers adjacent to horizontal bars indicate positions of molecular weight markers (kilodaltons). Lanes: 1, Sporadic CJD (PRNP genotype MM) type 1; 2, iatrogenic (growth hormone related) CJD (PRNP genotype MM) type 1; 3 and 4, sporadic CJD (PRNP genotype MM) type 2; 5, iatrogenic (dura mater related) CJD (PRNP genotype MM) type 2; 6 and 7, iatrogenic (growth hormone related) CJD (PRNP genotype VV) type 3; 8, iatrogenic (growth hormone related) CJD (PRNP genotype MV) type 3; 9, sporadic CJD (PRNP genotype MV) type 2; 10, "new variant" CJD (PRNP genotype MM) type 4.

FIG. 3 shows transmission of CJD to transgenic mice expressing only human PrP. Western blots of primary human inocula and mouse brain homogenates following treatment with proteinase K using the anti-PrP monoclonal antibody 3F4. Numbers adjacent to horizontal bars indicate positions of molecular weight markers (kilodaltons). "Hu" indicates human inocula, "Mo" indicates transgenic mice that developed disease following inoculation with this human case. Numbers adjacent to horizontal bars indicate positions of molecular weight markers (kilodaltons). Lanes 1 and 2, sporadic CJD (MV) type 2→mouse type 2; lanes 3 and 4, sporadic CJD (MV) type 2→mouse type 2; lanes 5 and 6, iatrogenic (growth hormone related) CJD (MM) type 1→mouse type 2; lanes 7 and 8, sporadic CJD (MM) type 1→mouse type 2; lanes 9 and 10, sporadic CJD (M) type 1→mouse type 2; lanes 11 and 12, sporadic CJD (VV) type 2→mouse type 2; lanes 13 and 14, iatrogenic (gonadotrophin related) CJD (VV) type 3→mouse type 3; lanes 15 and 16, iatrogenic (dura mater related) CID type 2→mouse type 2.

FIG. 4 shows the proportions of different PrP glycoforms in type 1, type 2, type 3 and type 4 ("new variant") CJD. % of each form are given as mean ±s.e.m of the three banding types. H=high molecular weight glycoform, L=lower molecular weight glycoform, U=unglycosylated. Results (%) were as follows: High MW: type 1, 25.7±2.6 (n=6); type 2, 25.2±0.7 (n=18); type 3, 28.4±1.2 (n=4); "new variant" CJD ("type 4"), 47.8±1.1 (n=9). Low MW: type 1, 41.9±2.2; type 2, 45.7±0.7; type 3, 44.2±1.3; type 4, 37.8±0.7. Unglycosylated: type 1, 32.5±1.3; type 2, 29.1±0.9; type 3, 27.4±2.3; type 4, 14.3±1.3. Differences between type 1 and type 2 were significant with respect to the low MW glycoform ($P<0.05$) but not with the high MW glycoform or unglycosylated form. There were no significant differences between types 1 and 3 and between types 2 and 3. All three bands were highly significantly different between type 4 and type 1, type 2 and type 3 (high MW glycoform each case P<0.0001). In all cases unpaired 2-tailed t-tests were performed.

FIG. 5 shows a scattergraph of proportions of protease resistant PrP in the high molecular weight and low molecular weight glycoform in individual human cases and animals with transmitted CID or naturally or experimentally transmitted BSE. (a) Comparison of sporadic, iatrogenic and "new variant" CJD. Type 1 CJD is represented by black squares, type 2 by white squares, type 3 by crosses and type 4 ("new variant" CJD) by white diamonds. (b) Comparison of CJD types with naturally and experimentally transmitted BSE. All sporadic and iatrogenic CJD (types 1–3) are represented by black squares, and "new variant" cases are represented by white circles. CJD transmissions to FVB mice are denoted by white squares, BSE transmissions to FVB and C57BL/6 mice by crosses and black circles respectively. Naturally transmitted BSE in a domestic cat is denoted by a black triangle and experimental BSE in macaque by a black diamond shape.

FIG. 6 shows the transmission of BSE to wild type C57BL/6 and FVB mice. Western blot of brain homogenates following pre-treatment with proteinase K using anti-PrP antibody R073. Numbers adjacent to horizontal bars indicate positions of molecular weight markers (kilodaltons). Lanes 1–3, C57BL/6 mice; lanes 4–8, FVB mice.

Figure 7:
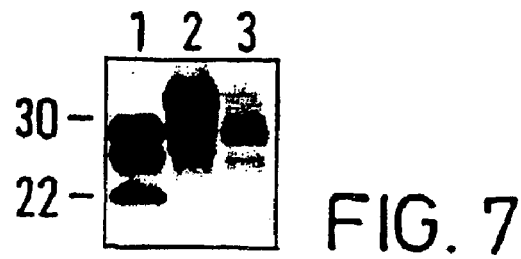

FIG. 7 shows a western blot of brain homogenates from a BSE-inoculated macaque (lane 1) using antibody R073 following pre-treatment with proteinase K and of a domestic cat with feline spongiform encephalopathy (lanes 2 and 3, before and after treatment with proteinase K respectively). Numbers adjacent to horizontal bars indicate positions of molecular weight markers (kilodaltons).

Figure 8A:
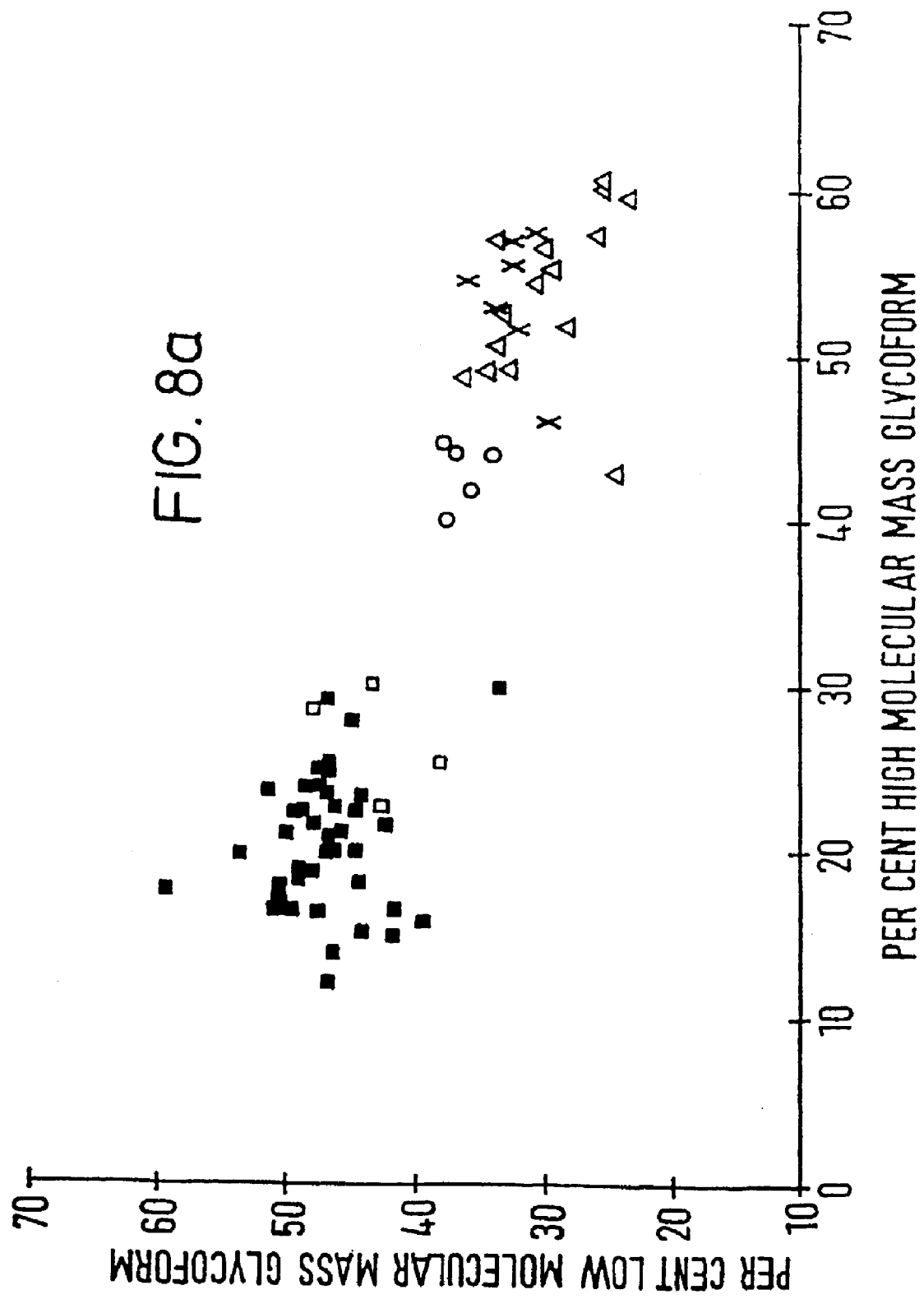
Figure 8B:
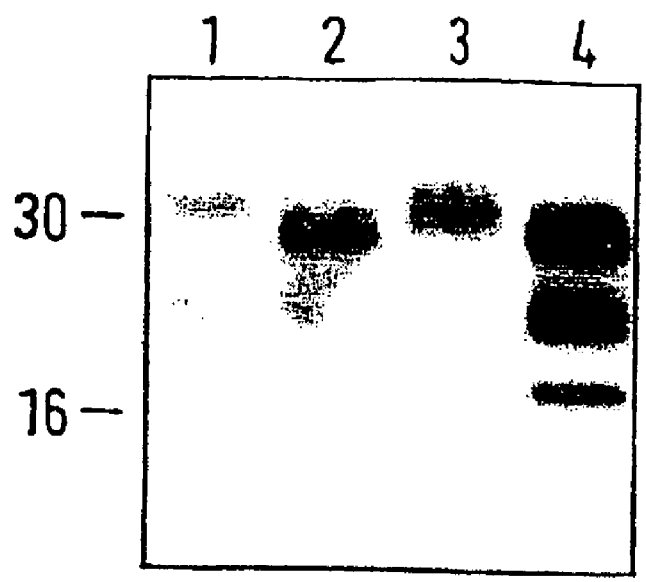
Figure 8C:
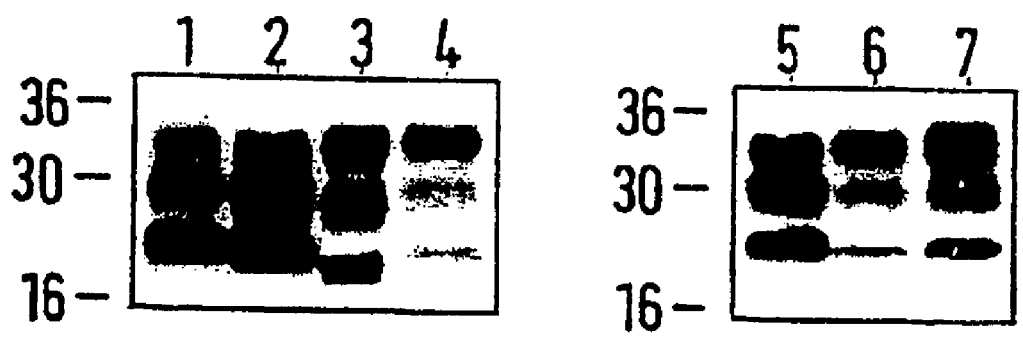

FIG. 8 shows the transmission of prion diseases to mice. a, Scatter graph of proportions of protease-resistant PrP in the high-molecular-mass (di-glycosylated) and low-molecular-mass (mono-glycosylated) glycoforms in individual human cases and FVB mice with experimentally transmitted CJD, vCJD or BSE. Sporadic and iatrogenic CJD cases PrP$^{Sc}$ types 1–3), black squares; vCJD, white circles; transmissions of typical CJD to FVB mice, white squares; BSE to FVB mice, crosses. Transmissions of vCJD to FVB mice, white triangles. b, c, Western blots of brain homogenates after pre-treatment with proteinase K using anti-PrP polyclonal antibody 95–108 (ref.44) (b) or anti-PrP monoclonal antibody 3F4 (c). Methods were as in ref. 43 except that for PrP glycoform analysis a chemifluorescent substrate (ECF, Amersham) was used and ratios analysed on a Storm 840 Phosphoimager (Molecular Dynamics). b, Transmission of vCJD and BSE to non-transgenic FVB mice. Lane 1, human VCJD; 2, vCJD-inoculated FVB mouse (same case as lane 1); 3, BSE; 4, BSE-inoculated FVB mouse (same case as in lane 3). c, Transmission of vCJD to HuPrP$^{+/+}$ Prn-p$^{0/0}$ transgenic mice. Lane 1, human CJD, type-2 PrP$^{Sc}$, 2, transgenic mouse inoculated with CJD case from lane 1 showing type-2 pattern; 3, human vCJD case, type4 PrP$^{Sc}$ transgenic mouse inoculated with vCJD from lane 3 showing type-5 pattern; human CJD case, type-2 PrP$^{Sc}$, 6 and 7, type-5 Prp$^{Sc}$ pattern in vCJD-inoculated transgenic mice.

Figure 9:
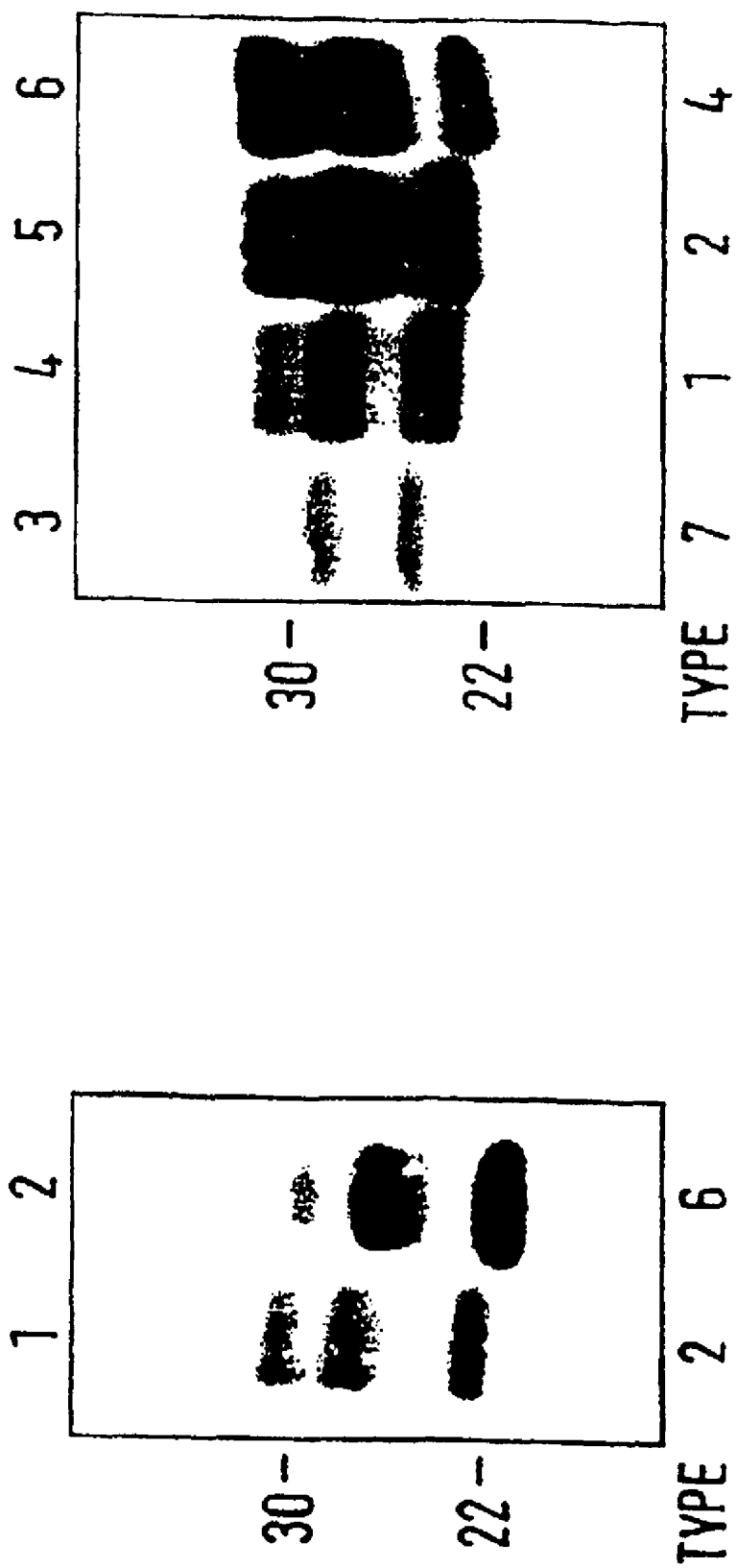

FIG. 9 shows western blots of proteinase K treated samples from patients with CJD, using anti-PrP monoclonal antibody 3F4. Numbers adjacent to horizontal bars indicate positions of molecular weight markers (kilodaltons). Lanes: 1, CJD strain type 2; 2, CJD strain type 6; 3, CJD strain type 7; lanes 4, 5 and 6, CJD strain types 1, 2 and 4 respectively.

EXAMPLES

Example 1

Methods

Selection and Molecular Genetic Analysis of Patients

Twenty six neuropathologically confirmed sporadic CJD cases including all three codon 129 genotypes, six neuropathologically confirmed iatrogenic CJD cases and ten neuropathogically confirmed "new variant" CJD cases referred to the National CJD Surveillance Unit or the Prion Disease Group on which frozen brain tissue was available for study were studied. Brain samples used were cerebral cortex, usually frontal cortex. DNA was extracted from blood or brain tissue and analysed for the presence of known or novel coding mutations in the prion protein gene (PRNP) and to determine codon 129 genotype. In 8/10 "new variant" CJD and the majority of sporadic and iatrogenic CJD patients, the complete PRNP open reading frame was PCR amplified using oligonucleotide primers chosen so as not to overlay an intron polymorphism 5' to the open reading frame which can lead to non-amplification of certain alleles, as described previously[35]. PCR product was size fractionated in agarose gels to exclude insertional or deletional mutations and PCR products were then sequenced on both DNA strands using an ABI 373 or 377 automated DNA sequencer.

Western Blot Analysis

Between 10 and 20 mg of brain tissue was homogenised in lysis buffer (0.5% NP40, 0.5% sodium deoxycholate in phosphate buffered saline) by serial passage through needles of decreasing diameter. The homogenate was cleared by centrifugation at 2,000 rpm for 5 minutes. Proteinase K (BDH) was added to a final concentration of 50μg/ml and the samples incubated at 37° C. for 1 hour. The reaction was terminated by the addition of Pefabloc (Boehringer) to 1 mM. The samples were mixed with 2×SDS loading buffer (125 mM tris-HCl, 4% SDS, 20% glycerol, 0.02% Bromophenol Blue, pH 6.8) and boiled for 10 minutes. They were then centrifuged at 14,000 rpm in a microfuge for 5 minutes before electrophoresis. Between 1 and 20 μl of sample was electrophoresed on 16% tris-glycine gels (Novex)[36]. The gels were then electroblotted onto PVDF membrane (Millipore) using either a tank or semi-dry blotting system[37]. The membranes were blocked in 5% BLOTTO (5% non fat milk powder in PBS with 0.05% Tween 20) for 1 hour at room temperature. After washing in PBST (PBS with 0.05% Tween 20) the membranes were incubated with anti-PrP monoclonal antibody 3F4[38] (diluted 1:5,000 in PBST) or rabbit polyclonal antibody R073[39] (diluted 1:10,000 in PBST) for between 1 hour and overnight. Following washing, the membrane was incubated with a horseradish peroxidase conjugated rabbit anti-mouse antibody (Sigma) or goat anti-rabbit antibody (Sigma) at a dilution of 1:10,000 in PBST for 1 hour. The membranes were washed again in PBST and developed using a chemiluminescent substrate (ECL; Amersham) using Biomax MR film (Kodak).

Deglycosylation of Prion Proteins

25 μl of 10% brain homogenate pre-treated with proteinase K was denatured in 0.5% SDS, 1% β-mercaptoethanol for 10 minutes at 100° C. NP-40 was added to 1% and the proteins were incubated in 500 units PNGaseF (New England Biolabs), using the proprietary buffer, at 37° C. for 2 hours. Following digestion, proteins were precipitated with 4 volumes of methanol and resuspended in SDS leading buffer and Western blotted as above.

Quantitation of PrP Glycoform Ratios

Blots were scanned on a Hoefer scanning densitometer (model GS300) and the relative amounts of the different glycoforms were obtained by computerised integration of peaks representing each of the three distinct bands. Scanning was performed on exposures within the linear range of the photographic film.

Transmission Studies in Transgenic and Non-transgenic Mice

Strict biosafety protocols were followed. Transgenic mice expressing human PrP were bred and maintained in an animal microbiological containment level I facility and moved to a containment level II facility where intracerebral inoculation was performed in a Class I microbiological safety cabinet. Preparation of inocula and removal of tissues was performed in a microbiological containment level III facility. All mice were examined twice weekly for the development of clinical signs of scrapie. At onset of signs mice were examined daily. Mice were culled if exhibiting any signs of distress. Criteria for clinical diagnosis of scrapie in mice were as described previously[40]. Transgenic lines expressing human PrP but not murine PrP were established by breeding mice transgenic for human PrP (designated Tg152, produced as described previously[25]) with mice homozygous for PrP null alleles[41]. All mice were genotyped to confirm presence of the HuPrP transgene or PrP null alleles by polymerase chain reaction (PCR) with genomic DNA obtained by tail biopsy as described[42]. Tg152 mice have expression levels of human PrP of 200% of that seen in normal human brain[42]. Mice were anaesthetised with halothane/$O_2$ and intracerebrally inoculated into the right parietal lobe with 30 µl of a 1% brain homogenate in phosphate buffered saline (PBS).

Example 2

Distinct prion strains are distinguished by their biological properties on transmission to laboratory animals and by physical and chemical differences in $PrP^{Sc}$ strains. We now find that the biological and molecular transmission characteristics of vCJD are consistent with it being the human counterpart of BSE.

We studied transgenic mice expressing only human PrP (HupRP$^{+/+}$ Prn-p$^{0/0}$), which have been shown to lack a species barrier to human prions from one iatrogenic CJD case, comparing them with non-transgenic (FVB) mice. All of 16 further CJD cases, encompassing a wide range of clinicopathological phenotypes, all three $PrP^{Sc}$ types reported in sporadic and acquired prion diseases and all PRNP genotypes at polymorphic codon 129, a key determinant of genetic susceptibility to human prion diseases were transmitted to these transgenic mice.

Almost all inoculated transgenic mice contracted disease with similar short incubation periods, consistent with a lack of species barrier to these isolates (Table 2). These transgenic mice express human PrP homozygous for valine at codon 129. However, there was no significant difference in mean incubation periods between inocula of the different codon 129 genotypes. $PrP^{Sc}$ typing of these transmissions showed that the same prion types seen in sporadic and iatrogenic CJD (types 1–3) are produced, distinct from that seen in vCJD (type 4). Only occasional transmissions, at longer and variable incubation periods, were seen in FVB mice.

In contrast, efficient transmission of vCJD to FVB mice was observed (Table 2) although incubation periods were prolonged. Conversely, the attack rate of vCJD in the transgenic mice was reduced in comparison to typical CJD, and incubation periods were generally more viable and prolonged. Mean incubation periods to these six vCJD cases were similar in both types of mice. The clinical course in vCJD-inoculated transgenic mice was much longer than in transmissions of typical CJD. vCJD in humans is also associated with a long clinical duration. Some mice, as well as showing typical neurological features, persistently walked backwards. This unusual clinical sign was not seen in transmissions of typical CJD, fatal familial insomnia or other inherited prion diseases.

BSE transmits efficiently to FVB mice, albeit with prolonged and variable incubation periods (Table 2) which fall to a consistent short incubation period of around 140 days on second passage (data not shown). Transmissions of BSE into the transgenic mice did not occur at incubation periods well beyond those of classical CJD, but we have now observed transmission with much longer incubation periods (Table 2). These transmissions resembled those of vCJD with a long clinical duration and backwards walking in some animals as well as the otherwise typical clinical features of mouse scrapie.

There were striking similarities in PrP deposition patterns between BSE- and vCJD-inoculated animals (detailed neuropathological studies will be published elsewhere). Such patterns are determined by host genotype as well as by agent strain. We saw distinct patterns in the two types of mice, but, in each case, vCJD and BSE produced closely similar patterns. In CID- and BSE-inoculated non transgenic mice, there were PrP plaques and diffuse PrP deposition. In CJD- and BSE-inoculated HuPrP$^{+/+}$ Prn-P$^{0/0}$ transgenic mice we saw a predominantly pericellular pattern of PrP immunostaining (data not shown). PrP plaques are a rare feature of prion disease in mice. Occasional mock-inoculated transgenic mice showed weaker and less extensive pericellular PrP immunostaining, probably reflecting the high level of $PrP^C$ overexpression in these mice. Western blotting for $PrP^{Sc}$ was negative in all these controls.

We performed western blot analysis to determine the $PrP^{Sc}$ types produced in these transmissions. We have previously shown that the $PrP^{Sc}$ type seen in vCJD (type 4) has a ratio of glycoforms closely similar to that of BSE passaged in several other species[2]. vCJD-inoculated FVB mice produced mouse $PrP^{Sc}$ with type [4]-like glycoform ratios and fragment sizes indistinguishable from those in BSE-inoculated FVB mice (FIG. 1a,b).

In transmission of vCJD to HuPrP$^{+/+}$ Prn-p$^{0/0}$ transgenic mice, where human $PrP^{Sc}$ is generated, fragment sizes in inoculum can be directly compared. Again the $PrP^{Sc}$ produced had type 4-like glycoform ratios. However, the fragment sizes differ from those in the inoculum and were indistinguishable from those in the type-2 $PrP^{Sc}$ pattern (FIG. 1c). We have designated this new pattern type 5.

A change of fragment size on passage in mice of a different codon 129 PrP genotype than the inoculum has been reported previously. Type-1 $PrP^{Sc}$, seen in CJD cases of 129MM PRNP genotype, consistently converts to type-2 $PrP^{Sc}$ on passage in these transgenic mice expressing 129VV human PrP. The glycoform ratios of the original inoculum are also maintained[2]. Abrupt changes in the biological properties ('mutation') of murine scrapie strains on passage in mice of different genotypes are well recognized. We have not, however, been able to show $PrP^{Sc}$ by Western blotting in BSE-inoculated HuPrP$^{+/+}$ Prn-p$^{0/0}$ transgenic mice. This may reflect culling of many of these mice soon after clinical diagnosis rather than at a more advanced clinical stage. Though transmission of prion diseases without detectable $PrP^{Sc}$ on primary passage has been reported, it will be important to confirm transmission by second passage studies.

The prion titres in these primary inocula are unknown but may be higher in the human cases, because cattle with BSE will have been culled before the terminal stages of disease. However, on clinical, pathological and molecular criteria, vCJD shows remarkable similarity in its transmission characteristics to BSE, and is quite distinct from all other forms of sporadic and acquired CJD. These data provide compelling evidence that BSE and vCJD are caused by the same prion strain. Taken together with the temporal and spatial association of vCJD with BSE but not with scrapie or other animal prion diseases, and BSE transmission studies in macaques, this strongly suggests that vCJD is caused by BSE exposure. The theoretical possibility that both BSE and vCJD arise from exposure to a common unidentified source appears remote.

The production of a distinct molecular strain type on transmission of vCJD to mice expressing valine 129 human PrP suggests that BSE transmitted to humans of this genotype might produce a similar strain. Such cases may differ in their clinical and pathological phenotype to vCJD, but could be identified by $PrP^{Sc}$ typing.

Although it has been argued that the species barrier resides in PrP primary structure differences between donor and host, our data emphasize that strain type can be as important. As prion propagation involves interactions between $PrP^{Sc}$ and host $PrP^{C}$, and strains are associated with differences in PrP conformation and glycosylation, such PrP interactions may be most efficient if the interacting proteins are not only of the same sequence but have similar conformational preferences and glycosylation. Mismatch of codon 129 between inoculum and $HuPrP^{+/+}$ $Prn-p^{0/0}$ mice does not significantly affect CJD transmission, but this could differ for BSE. All vCJD cases have been 129MM genotype. Although our 129VV mice are much less susceptible to BSE than to typical CJD, suggesting a substantial species barrier, 129MM human PrP mice could be more susceptible.

Example 3

Samples from 100 CJD patients were $PrP^{Sc}$ typed according to the methods already described above. Accordingly two new distinct patterns of protease resistant PrP on Western blots can be identified. These are named types 6 and 7 (FIG. 9) and are believed to be additional sub-types of classical CJD.

REFERENCES

1. Prusiner, S. B. *Science* 252, 1515–1522 (1991).
2. Caughey, B. & Raymond, G. J. *J Biol. Chem.* 266 No 27, 18217–18223 (1991).
3. Pan, K.-M., Baldwin, M., Nguyen, J., et al. *Proc. Natl. Acad. Sci. USA* 90, 10962–10966 (1993).
4. Prusiner, S. B., Scott, M., Foster, D., et al. *Cell* 63, 673–686 (1990).
5. Weissmann, C. *Nature* 349, 569–571 (1991).
6. Palmer, M. S., Dryden, A. J., Hughes, J. T. & Collinge, J. *Nature* 352, 340–342 (1991).
7. Kocisko, D. A., Come, J. H., Priola, S. A., et al. *Nature* 370, 471–474 (1994).
8. Wells, G. A. H. & Wilesmith, J. W. *Brain Pathol.* 5, 91–103 (1995).
9. Bruce, M., Chree, A., McConnell, I., Foster, J., Pearson, G. & Fraser, H. *Philos. Trans. R. Soc. Lond. [Biol.]* 1343, 405–411 (1994).
10. Collinge, J., Palmer, M. S., Sidle, K. C. L., et al. *Nature* 378, 779–783 (1995).
11. Bruce, M. E., Fraser, H., McBride, P. A., Scott, J. R. & Dickinson, A. G. in *Prion Diseases in Human and Animals* (eds Prusiner, S. B., Collinge, J., Powell, J. & Anderton, B.) Ellis Horwood, London, 1992).
12. Marsh, R. F. & Kimberlin, R. H. *J Infect. Dis.* 131, 104–110 (1975).
13. Bessen, R. A. & Marsh, R. F. *J. Virol.* 66, 2096–2101 (1992).
14. Bessen, R. A. & Marsh, R. F. *J. Virol.* 68, 7859–7868 (1994).
15. Bessen, R. A., Kocisko, D. A., Raymond, G. J., Nandan, S., Lansbury, P. T. & Caughey, B. *Nature* 375, 698–700 (1995).
16. Windl, O., Dempster, M., Estibeiro, J. P., et al. *Hum. Genet.* 98, 259–264 (1996).
17. Weller, R. O. *Psychol. Med.* 19, 1–4 (1989).
18. Baker, H. F., Poulter, M., Crow, T. J., et al. *Lancet* 337, 1286(1991).
19. Collinge, J., Palmer, M. S. & Dryden, A. J. *Lancet* 337, 1441–1442 (1991).
20. Brown, P., Cervenakova, L., Goldfarb, M. D., et al. *Neurology* 44, 291–293 (1994).
21. Will, R. G., Ironside, J. W., Zeidler, M., et al. *Lancet* 347, 921–925 (1996).
22. Collinge, J., Beck, J., Campbell, T., Estibeiro, K. & Will, R. G. *Lancet* 348, 56(1996).
23. Parchi, P., Castellani, R., Capellari, S., et al. *Annals of Neurology* 39, 767–778 (1996).
24. Telling, G. C., Scott, M., Mastrianni, J., et al. *Cell* 83, 79–90 (1995).
25. Telling, G. C., Scott, M., Hsiao, K. K., et al. *Proc Natl Acad Sci USA* 91, 9936–9940 (1994).
26. Wyatt, J. M., Pearson, G. R., Smerdon, T. N., Gruffydd-Jones, T. J., Wells, G. A. H. & Wilesmith, J. W. *Vet. Rec.* 129, 233–236 (1991).
27. Lasmézas, C. I., Deslys, J.-P., Demaimay, R., et al. *Nature* 381, 743–744 (1996).
28. Brown, P., Preece, M. A. & Will, R. G. *Lancet* 340, 24–27 (1992).
29. Page, G. *Nature* 382, 381(1996).
30. Kimberlin, R. H. & Walker, C. A. *Virus Res.* 12, 201–211 (1989).
31. Schreuder, B. E. C., van Keulen, L. J. M., Vromans, M. E. W., Langeveld, J. P. M. & Smits, M. A. *Nature* 381, 563(1996).
32. Kimberlin, R. H. & Walker, C. A. *J Gen. Virol.* 69, 2953–2960 (1988).
33. Laplanche, J.-L., Delasnerie-Lauprêtre, N., Brandel, J. P., et al. *Neurology* 44, 2347–2351 (1994).
34. Hecker, R., Taraboulos, A., Scott, M., et al. *Gen. & Dev.* 6, 1213–1228 (1992).
35. Palmer, M. S., van Leeven, R. H., Mahal, S. P., Campbell, T. A., Humphreys, C. & Collinge, J. *Human Mutation* 7, 280–281 (1996).
36. Laemmli, U. K. *Nature* 227, 680–685 (1970).
37. Towbin, H., Staehelin, T. & Gordon, J. *Proc. Natl. Acad. Sci. U.S.A.* 76, 4350–4354 (1979).
38. Kascsak, R. J., Rubenstein, R., Merz, P. A., et al. *J Virol.* 61, 3688–3693 (1987).
39. Serban, D., Taraboulos, A., DeArmond, S. J. & Prusiner, S. B. *Neurology* 40, 110–117 (1990).
40. Carlson, G. A., Kingsbury, D. T., Goodman, P. A., et al. *Cell* 46, 503–511 (1986).
41. Bueler, H., Fischer, M., Lang, Y., et al. *Nature* 356, 577–582 (1992).
42. Whittington, M. A., Sidle, K. C. L., Gowland, I., et al. *Nature Genetics* 9, 197–201 (1995).
43. Collinge, J., Sidle, K. C. L., Meads, J., Ironside. & Hill, A. F. *Nature* 383, 685–690 (1996).
44. Piccardo, P. et al. J. Neuropathol. Exp. Neurol. 56, 589 (1997).

What is claimed is:

1. A method for typing a sample of a prion or spongiform encephalopathy disease the method comprising comparing and identifying similar physicochemical properties of the sample with a standard sample of known $PrP^{Sc}$ type, wherein the physicochemical properties are the sizes and ratios of distinct $PrP^{Sc}$ glycoforms.

2. A method as claimed in claim 1 wherein the standard sample of known $PrP^{Sc}$ type is bovine spongiform encephalopathy or Creuztfeldt-Jakob disease.

3. A method as claimed in claim 1 wherein the comparison of physicochemical properties comprises a comparison of protease resistance, fragment size, and ratio of $PrP^{Sc}$ glycoforms.

4. A method as claimed in claim 3 wherein the protease resistance is proteinase K resistance.

5. A method as claimed in claim 3 wherein the spongiform encephalopathy is derived from a mammal or derived from a chicken.

6. A method as claimed in claim 3 wherein the method comprises subjecting the sample to digestion by a protease, electrophoresing the result of the digestion and comparing the resulting pattern of fragment size and ratio of $PrP^{Sc}$ glycoforms of the electrophoresis with a standard electrophoresis pattern of a known $PrP^{Sc}$ type.

7. A method as claimed in claim 3 wherein the typing of the sample comprises a method of diagnosing a disease.

8. A method as claimed in claim 6 wherein the sample to be typed is derived from a mammal or derived from a chicken.

9. A method as claimed in claim 3 wherein the sample to be typed is derived from brain tissue, other central nervous system tissue, a tissue of the lymphoreticular system, cerebrospinal fluid and/or the blood.

10. A method as claimed in claim 6 wherein the electrophoresis pattern of the known sample has a pattern substantially similar to that of type 4 as shown in FIG. 4.

11. A method of identifying a bovine spongiform encephalopathy infection in an animal and/or tissue, the method comprising isolating a prion protein from the animal and/or tissue and identifying that said prion protein is characterized by having three distinct bands on an electrophoresis gel following proteinase K digestion, the bands comprising (i) a band of highest molecular weight in the greatest proportion, (ii) a band of lowest molecular weight in the lowest proportion, and (iii) a band with a molecular weight between the bands of (i) and (ii) and a proportion between the bands of (i) and (ii) and by having substantially similar glycoform proportions as bovine spongiform encephalopathy.

12. A method as claimed in claim 11 wherein the animal or tissue is non-bovine.

13. A method as claimed in claim 11 wherein the animal, and/or tissue, from which the prion is sampled is derived from a mammal or derived from a chicken.

14. A method as claimed in claim 11 wherein the prion is derived from brain tissue, other central nervous system tissue, a tissue of the lymphoreticular system, cerebrospinal fluid and/or the blood.

15. A method for identifying infection in an animal and/or tissue, as claimed in claim 11, wherein the electrophoresis pattern of the known sample has a pattern substantially similar to that of type 4 as shown in FIG. 4.

16. The method of claim 5, wherein the spongiform encephalopathy is selected from the group consisting of bovine, feline, cervine, ovine, human, primate, and murine.

17. The method of claim 8, wherein the spongiform encephalopathy is selected from the group consisting of bovine, feline, cervine, ovine, human, primate, and murine.

18. The method of claim 13, wherein the spongiform encephalopathy is selected from the group consisting of bovine, feline, cervine, ovine, human, primate, and murine.

19. The method of claim 9, wherein the prion is derived from a tissue of the lymphoreticular system selected from the group consisting of spleen, tonsil, and lymph node.

20. The method of claim 14, wherein the prion is derived from a tissue of the lymphoreticular system selected from the group consisting of spleen, tonsil, and lymph node.

* * * * *